United States Patent [19]

Hickman

[11] Patent Number: 4,824,368
[45] Date of Patent: Apr. 25, 1989

[54] ORAL HYGIENE APPLIANCES

[75] Inventor: Clarence J. Hickman, Ft. Collins, Colo.

[73] Assignee: Teledyne Industries, Inc., Fort Collins, Colo.

[21] Appl. No.: 410,257

[22] Filed: Aug. 23, 1982

[51] Int. Cl.⁴ .............................................. A61G 17/02
[52] U.S. Cl. ..................... 433/80; 128/62 A
[58] Field of Search ................. 433/80; 128/62 A, 66

[56] References Cited

U.S. PATENT DOCUMENTS 3,227,158  1/1966  Mattingly .............................. 128/62
4,302,186  11/1981  Cammack et al. ..................... 433/80

FOREIGN PATENT DOCUMENTS 2545936  4/1977  Fed. Rep. of Germany .
2910982  2/1980  Fed. Rep. of Germany .
1182031  2/1970  United Kingdom .

Primary Examiner—Gene Mancene
Assistant Examiner—James R. Hakomaki
Attorney, Agent, or Firm—Hugh H. Drake

[57] ABSTRACT

An oral hygiene device includes a supply of liquid, a pump for propelling the to a point of use. A housing defines a cavity within which the pump is seated and which also includes an inlet and an outlet. The pump is of a kind having a hollow body with a chamber defined in a first portion, a piston disposed for reciprocation in that chamber and a motor to drive the piston and thereby the pump. A second portion of the body is coupled to an outlet. A third portion of the body is coupled to an inlet. A first check valve is at least effectively disposed in a third portion of the body and poled to pass liquid only from the inlet to the chamber. A second check valve is at least effectively disposed in the second portion of the body and is poled to pass liquid only from the chamber to the outlet.

2 Claims, 5 Drawing Sheets

ORAL HYGIENE APPLIANCES

The present invention pertains to oral hygiene appliances. More particularly, it relates to improvements in a pumping system.

Much of the disclosure presented in this application is the same or very similar to U.S. Pat. No. 4,302,186, filed in the names of Michael A. Cammack, Christopher W. Elkins, Clarence J. Hickman and Keith M. Mullins and assigned to Teledyne Industries, Inc. In view of the close correspondence of many of these structural features, the disclosure of that patent is referred to and incorporated herein by reference. Because dates do not overlap, that earlier patent will be referred to herein as the "senior patent" even though it does not have a parent-to-child relationship in terms of co-pending disclosure.

The oral hygiene appliance of the senior patent found concrete utility. The truly-portable unit there described achieved success in the marketplace. Unfortunately, a few problems developed as a result of the compacting of the appliance into a size that could be accommodated within a confined space. Those problems are believed to have now been resolved. The instant new disclosure will update some details of a preferred approach and yet which are not claimed and also other details which are newly claimed.

It is a general aim of the present application to disclose the solutions to at least some of those problems which have arisen.

Oral hygiene appliances of the kind in question employ a piston-type pumping stroke. In attempting to reduce size, the stroke length was reduced in the version disclosed in the senior patent. That reduction in stroke length has led to a tendency in the unit for failure of the pump to prime itself when first starting. That is, the reciprocating-type of pump tends to feed back air from the outlet rather than pumping the desired liquid. This problem appears to be worsened by the fact that the supply of the reservoir of the liquid is similarly reduced in size. That reduces the pressure head upon the liquid.

It is, therefore, another object of the present invention to provide new and improved apparatus which solves such problems.

As before, the present invention involves a device that includes a supply of a liquid, a pump for propelling the liquids and means for delivering the propelled liquid to a point of use. A housing defines a cavity within which the pump is seated and there are means in the housing for defining both an outlet and an inlet. A motor is seated within the cavity for driving the pump. The pump has a hollow body with a chamber defined in a first portion thereof. Disposed for reciprocation in that chamber is a piston. A motor is coupled to the piston for enabling reciprocation thereof. Second and third portions of the body are respectively coupled to the outlet and the inlet. A first check valve effectively is disposed in the third portion of the body and poled to pass liquid only from the inlet to the chamber. The second check valve is effectively disposed in the second portion of the body and is poled to pass liquid only from the chamber to the outlet.

The features of the present invention which are believed to be patentable are set forth with particularity in the appended claims.

The organization and manner of operation of the invention, together with further objects and advantages thereof, may best be understood by reference to the following description taken in connection with the accompanying drawings, in the several figures of which like numerals identify like elements, and in which.

Figure 1:
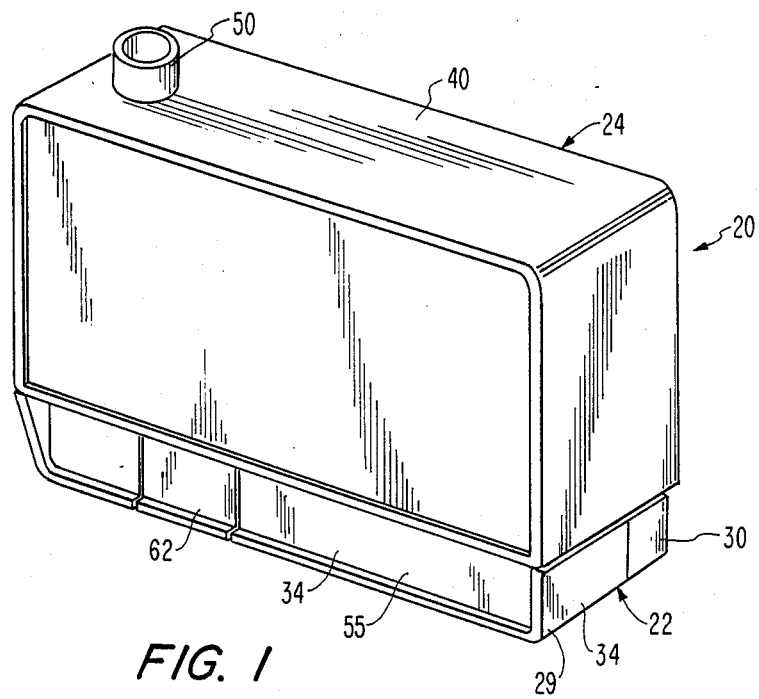
FIG. 1 is an isometric view of an oral hygiene appliance with a reservoir disposed in a storage position on a housing.

An oral hygiene appliance or device 20 includes a housing 22 associated with a reservoir 24 and nozzles 26. In use, reservoir 24 contains a supply of water or other liquid that is supplied to and propelled by a pump 28, located within housing 22, and delivered by a selected one of nozzles 26 to the point of use within a person's mouth for cleaning the teeth and massaging the gums.

Figure 4:
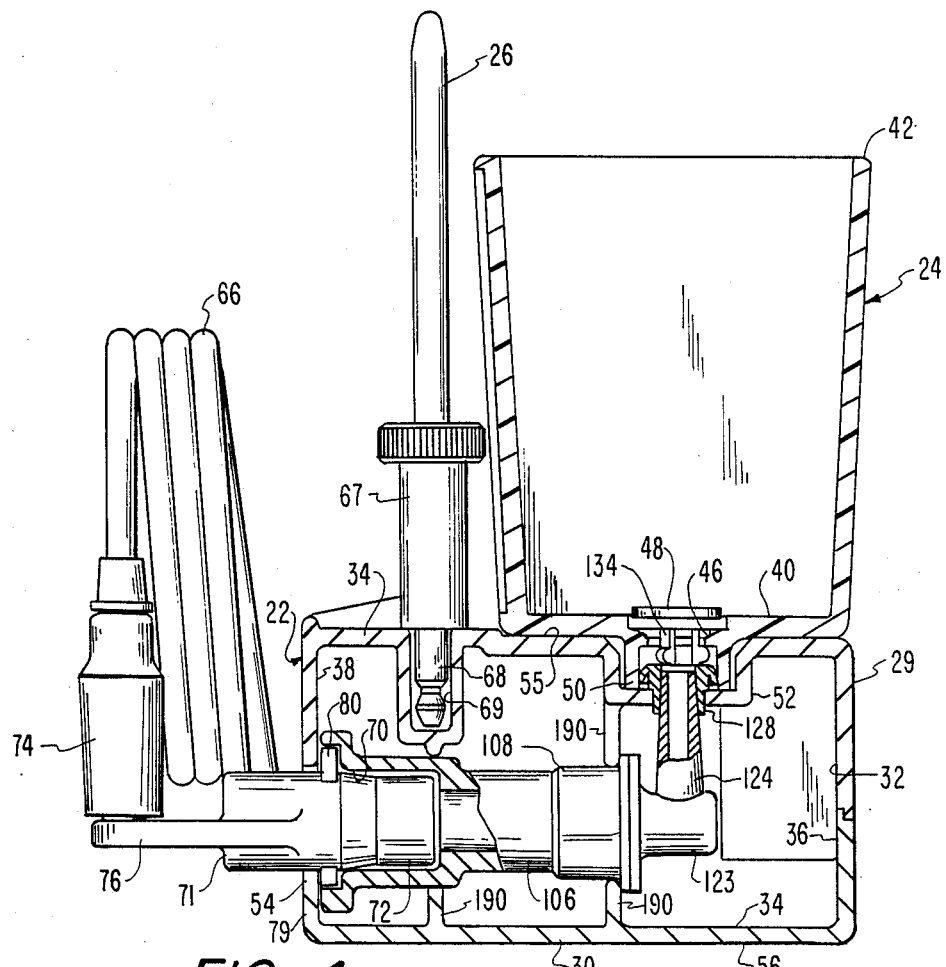
FIG. 4 is a cross-sectional view taken along the line 4—4 in FIG. 2.

Housing 22 is formed by shells 29 and 30 which mate together to define a cavity 32 thus bounded by a surrounding wall 34 and opposing end walls 36 and 38, using FIG. 4 for reference as to "end". Reservoir 24 is closed at one end 40 and open at its other end 42. As shown in FIG. 1, reservoir 24 has a shape which is conformity with housing 22, so as to telescope thereover in covering relationship with most of surrounding wall 34 and its end wall 36 for storage when the appliance is not in use and for convenience during transport.

Figure 5:
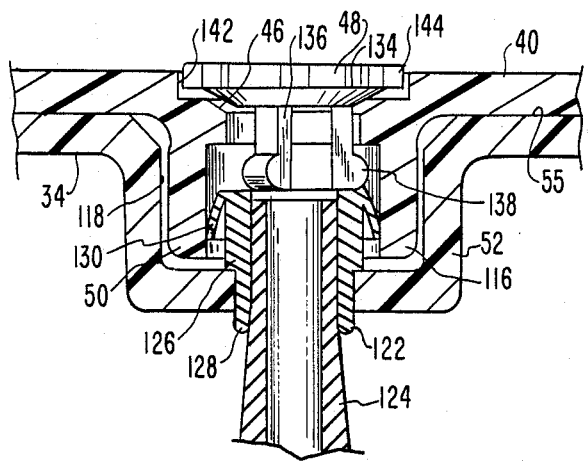
FIG. 5 is a fragmentary and enlarged cross-sectional view of a fluid coupling assembly shown in FIG. 4.

Defined in reservoir end 40 is a valve seat 46 that cooperates with a valve 48. The valve is normally closed to the valve seat when reservoir 24 contains water and is removed from its telescopically covering relationship with housing 22. In liquid communication with valve seat 46 on end 40 of reservoir 24 is a coupling 50. Matable with the latter in further liquid communication is a coupling member 52 disposed in surrounding wall 34 of housing 22 upon placement of reservoir end wall 40 adjacent to surrounding wall 34 and in a position to overlie member 52 (FIGS. 4 and 5).

Disposed in end wall 38 of housing 22, for communication with nozzle 26, is an outlet opening 54 that is so located as to be free of any part of reservoir 24 when the latter is placed in its aforementioned covering relationship with respect to the housing. Pump 28 is disposed within cavity 32 and connected between coupling member 52 and outlet opening 54.

Figure 2:
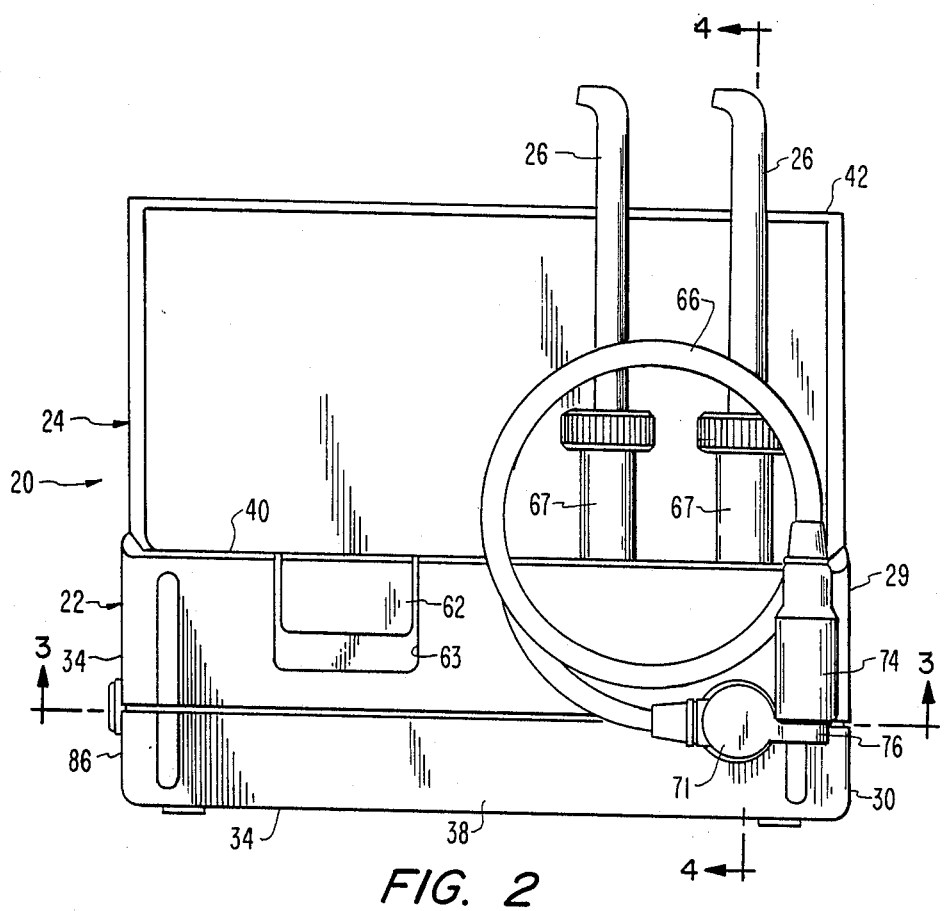
FIG. 2 is a front elevational view of the appliance with the reservoir and housing in operative positions and with additional components mounted on the housing.

It will be observed that surrounding wall 34 is of generally rectangular cross section, so as to have space-opposed generally-planar panels 55 and 56 along longer sides of that cross section. For use, as shown in FIGS. 2 and 4, reservoir 24 is to be placed with its end wall 40 adjacent to the upper panel 55, and the other opposed panel 56 serves as a supporting base for the entire device as when resting on a countertop or the like.

Seated within cavity 32 is an electric motor 58 connected to drive pump 28 and associated with a switch 60 for energizing the motor. Switch 60 includes an operator or button 62 disposed in shell 29 of housing 22 in a location which is free of all portions of reservoir 24 when the latter is placed in position for use as shown in FIGS. 2 and 4. As shown in FIG. 2, button 62 is in its "off" position. When in its "on" position, button 62 is moved downwardly within a recess 63.

To be coupled between outlet opening 54 and one of nozzles 26 is a flexible hose 66. Each nozzle 26 projects through a base 67 formed at its lower end to receive the lower end 68 of the nozzle. Lower end 68 may be seated in one of recesses 69 formed into a portion of the upper panel of shell 29 that is free of reservoir 24 when the latter is situated for use. Thus, the nozzle assemblies may be stored alongside reservoir 24 when the reservoir is positioned in its use orientation.

Projecting inwardly from opening 54 in housing end wall 38, and in this case formed as an integral part of the structure which includes pump 28, is a well 70 that serves as part of connecting means for coupling the pump output into the bottom of well 70. Connected to the end of hose 66 that is to be opposite nozzle 26 is a plug 71 which is insertable removably into well 70 and is hollow so as to transmit liquid from pump 28 into hose 66. An O-ring 72 seals plug 71 within well 70.

Figure 8:
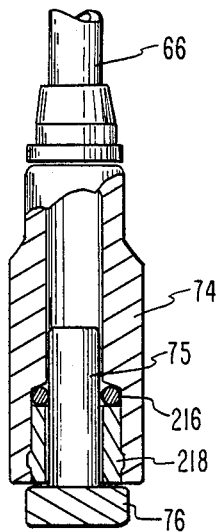
FIG. 8 is a fragmentary and enlarged cross-sectional view of a coupling element in a storage position as shown in FIGS. 2 and 4.
Figure 10:
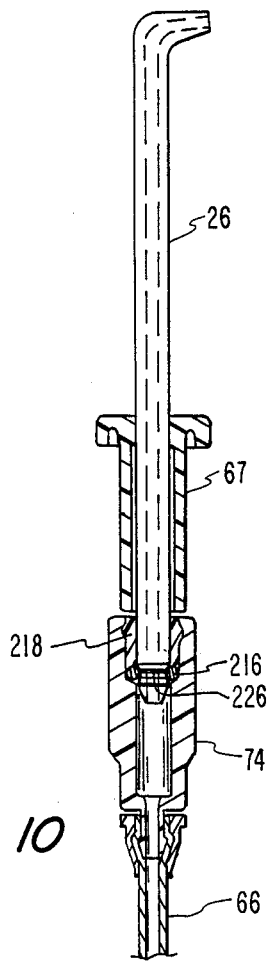
FIG. 10 is an enlarged and fragmentary cross-sectional view of coupling components shown in FIGS. 2 and 4 but fitted together in operative position.

Affixed on the other end of hose 66 is a hollow coupling 74 into which lower end 68 is seated during operation (FIG. 10). For temporary storage, on the other hand, coupling 74 may be seated on a post 75 that projects upwardly from a shelf 76 on plug 71 when the latter is inserted into well 70 (FIGS. 2, 4 and 8). A pair of oppositely spaced recesses 77 and 78 (FIG. 3) are defined at corresponding sides of opening 54 and formed lugs 79 and 80 (FIG. 4) project laterally from plug 71 and serve to permit insertion of plug 71 within opening 54 in only one appropriate rotational position. Recesses 77 and 78 cooperate with space-opposed detents 81. The housing wall is sufficiently flexible to provide a spring action so that lugs 79 and 80 are cammed over detents 81 and into a locked position upon insertion of plug 71 into place.

Also seated within cavity 32 is a battery 82 for energizing motor 58 and removably insertable through an opening 84 defined in a side wall portion 86 of surrounding wall 34. Opening 84 is closed by a cover plug 88.

Button 62 normally rests in a position which is flush with panel 55 of surrounding wall 34 and end wall 38 within which it is disposed, and the button is located to be free of reservoir 24 when either in its storage position as shown in FIG. 1 or in its use position as shown in FIGS. 2 and 4. In the orientation of FIG. 1, a portion on button 62 and outlet opening 54 in end wall 38 are concealed from view on the underside of the unit. On the other hand, coupling member 52 is disposed in panel 55 of surrounding wall 34 to be concealed from external view when reservoir 24 is inverted as in FIG. 1 to face its closed end 40 upwardly and is telescoped into covering relationship with housing 22 as end wall 38 rests on a substrate.

Figure 6:
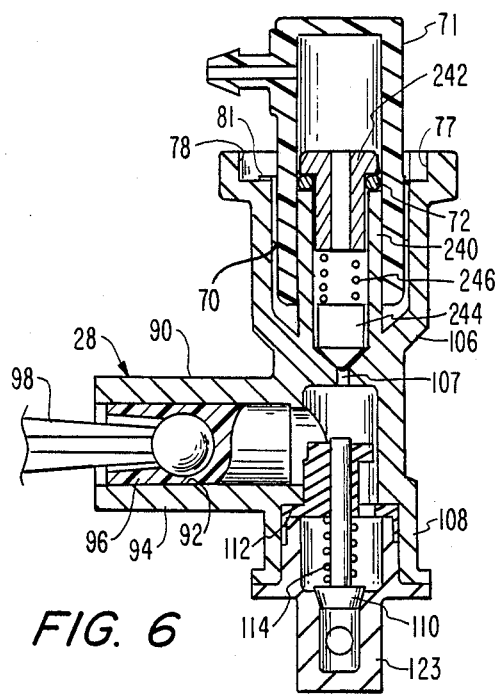
FIG. 6 is a fragmentary and enlarged cross-sectional view of a pump assembly and coupling shown in FIGS. 2-4.
Figure 7:
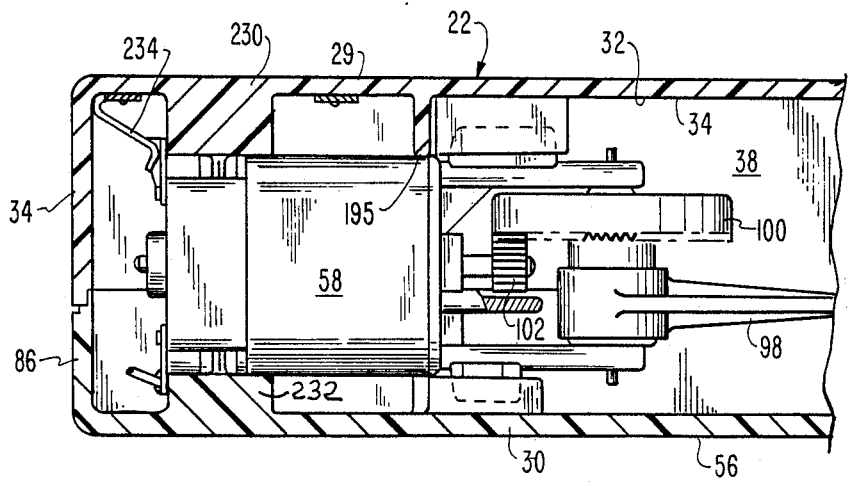
FIG. 7 is a fragmentary and enlarged cross-sectional view of a motor assembly shown in FIG. 3.

Pump 28 includes a generally T-shaped hollow body 90, and a chamber 92 is defined in its leg 94 (FIG. 6). Disposed for reciprocation within chamber 92 is a piston 96 coupled by a rod 98 eccentrically to a face gear 100 driven in rotation by a spur gear 102 on the output shaft of motor 58 (FIG. 7).

One arm 106 of pump body 90 is disposed at and effectively coupled to outlet 54 by an integral extension which defines well 70. Beneath well 70 in arm 106 is a cross-wall in which is defined an exit orifice 107. The other arm 108 of pump body 90 is coupled to member 52. A check valve 110, slidable within a valve guide 112, is disposed within arm 108 and poled by a compression spring 114 to pass liquid only from coupling member 52 and on into chamber 92 (FIG. 6). Valve guide 112 also forms a fluid seal.

Coupling element 50 includes a snout 116 that projects outwardly from end 40 of reservoir 24 and is aligned for liquid communication with valve seat 46. Coupling member 52 includes a well 118 defined in panel 55 of surrounding wall 34 and matable in liquid communication with snout 116 upon placement of end wall 40 against panel 55 of housing 22 and in a position to overlie well 118. An opening 122 is defined in the bottom of well 118. Coupled at one end to pump 28 and forming an integral lateral projection from an end cap 123 on arm 108 of pump body 90 is a tube 124. Tube 124 is disposed to project its free end through opening 122.

A seal 126 disposed within opening 122 includes a sleeve 128 seated between opening 122 and tube 124. Seal 126 also includes a skirt 130 that is flared away from sleeve 128 and into engagement with the interior wall of snout 116 when reservoir 24 is mounted as shown in FIGS. 4 and 5. Tube 124 is tapered in wall thickness as shown to cause sleeve 128 to flare outwardly on assembly and thereby become locked in position.

Valve 48 includes a tube-shaped operator portion 134 that faces the free end of tube 124 which serves as an abutment. That free end is disposed in a position to engage operator 134 and open valve 48 when end wall 40 of reservoir 24 is placed into the use position. Operator 134 is a coupler which moves inside valve seat 46. Included as a part thereof are a plurality of circumferentially-spaced resilient fingers 136 each of which has a laterally-facing lip 138 that is insertable through the inside of valve seat 46 to snap into place adjacent to the surface of reservoir end wall 40 opposite seat 46. Valve 48 is thereby captivated between open and closed positions.

Defined on the interior of end wall 40 of reservoir 24 is a recess 142 that surrounds valve seat 46. Included on valve 48 are a plurality of circumferential flutes 144 that face the internal wall of recess 142 and define therewith a strainer when valve 48 is open with respect to valve seat 46. That is, valve 48 is formed to combine in but one part the combination of both a strainer element and a valve element. Valve 48 is lifted only enough to open a fluid path between fingers 136, while yet creating a restriction against the passage into the pump body of any large particles of foreign matter.

Figure 11:
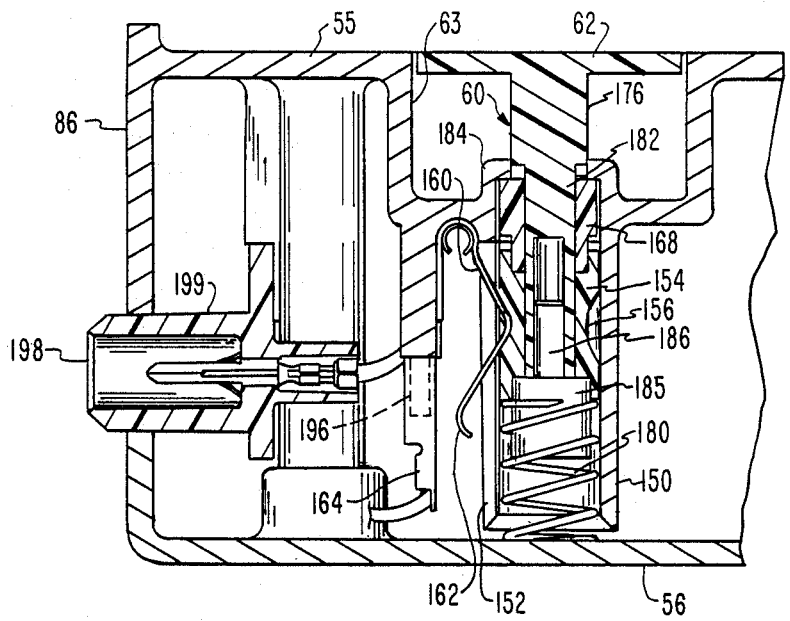
FIG. 11 is an enlarged and fragmentary cross-sectional view of an electrical switch and connector assembly shown in FIG. 3.
Figure 12:
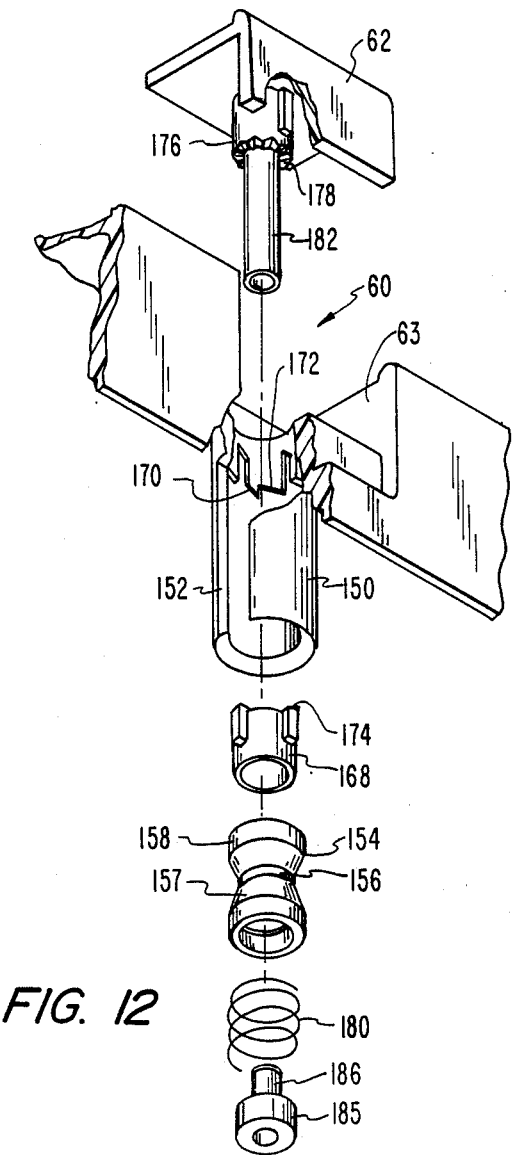
FIG. 12 is an exploded isometric view of the switch assembly shown in FIG. 11.

Button 62 is depressably mounted in its exposed position on housing 22. Defined within the housing is a barrel 150 beneath button 62 (FIGS. 11 and 12). An opening 152 is defined longitudinally through the wall of barrel 150. Slidable longitudinally within the barrel is a spool 154 that has a circumferential central V-shaped groove 156 to present a first surface 157 which faces opening 152 and is axially spaced from a second surface 158 on a remaining portion of the external wall of spool 154. That is, the bottom of groove 156 is spaced a different distance from opening 152 than is surface 158.

Spool 154 is movable axially within barrel 150 between first and second positions in alternate directions upon successive depressions of button 62. A resilient conductive finger 160 projects through opening 152 and against the exterior wall of spool 154. Movement of the spool between its first and second positions aligns respective different ones of groove 156 and surface 158 in engagement with finger 160, so as correspondingly to change locations of a contact portion 162 on finger 160. A conductive contact element 164 is disposed in the path of contact portion 162 and is engageable and disengageable with the latter upon its change between such locations. Contact portion 162 and contact element 164 are connected in circuit with motor 58 and battery 82.

Moving spool 154 between its two different positions is a rotatable cam cylinder 168 disposed within barrel 150 adjacent to spool 154. A plurality of cam operators 170 and stops 172 defined on and circumferentially spaced alternately around the inner wall of barrel 150 cooperate with cam surfaces 174 correspondingly circumferentially-spaced around the circumference of cylinder 168. Projecting inwardly from button 62 is a driver 176 on which are defined cam elements 178 that also cooperate with cam surfaces 174. A compression spring 180, disposed on the end of spool 154 opposite cylinder 168, urges spool 154, cylinder 168 and driver 176 together. Projecting integrally downward also from button 62, and having a diameter less than that of driver 176, is a spindle 182 upon which cylinder 168 and spool 154 are longitudinally slidable. Barrel 150 projects above the bottom of recess 63 as a boss 184, serving to prevent water that leaks around the edges of button 62 from entering the interior of the housing.

Differing from the structure of the senior patent, a frictionally inserted post 185 has a necked-down shaft 186 which is pressed into the interior of spool 154 in order to secure the internal switch parts into operative relationship and to hold button 62 in place (FIG. 11). Post 185 should fit sufficiently tight that at least a pull out force of four pounds is required to dislodge it.

The resulting switch combination operates in a manner similar in principle to that involved in connection with the push-push operation of one mechanism particularly employed in ball point pens for moving the reservoir and writing point within a barrel. Each depression of button 62 causes cylinder 168 to be rotated one step by driver 176 as a result of which the ends of cams 174 alternately are held downwardly against stops 172 and allowed to pass upwardly between cam operators 170. That alternate positioning serves correspondingly to cause the alternate opening and closing of contact member 162 with contact element 164. A principal difference from the mentioned mechanism employed in a ball-point pen resides in the separation of cylinder 168 from spool 154. Consequently, cylinder 168 is free to rotate even though spool 154 is under a side loading imposed by contact finger 160.

Figure 3:
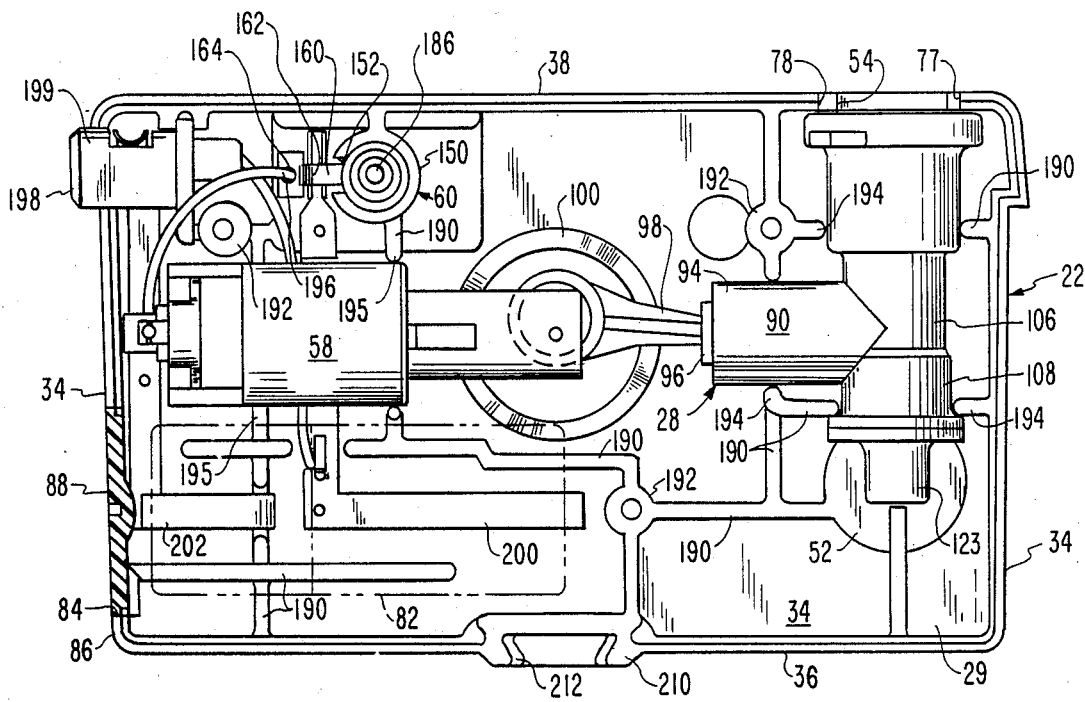
FIG. 3 is a cross-sectional view taken along the line 3—3 in FIG. 2, the additional components having been removed.

A plurality of integrally-formed webs 190 are disposed within each of shells 29 and 30 and arranged as shown in FIGS. 3 and 4 to define a plurality of compartments. Also projecting toward one another are a plurality of mating posts 192 that mate as between the respective shells so as to fasten them together upon the insertion of screws (not shown). Different ones of the wells as illustrated define appropriate recesses as at 194 so as to snugly captivate and seat pump body 90. Motor 58 is similarly seated and supported in a recess 195. Moreover, lugs on the frame of motor 58 are trapped by the webs that define recess 195. This constrains motor movement as against the forces resulting from the eccentric drive system for the pump unit. A projection 196 serves to mount contact element 164.

Figure 9:
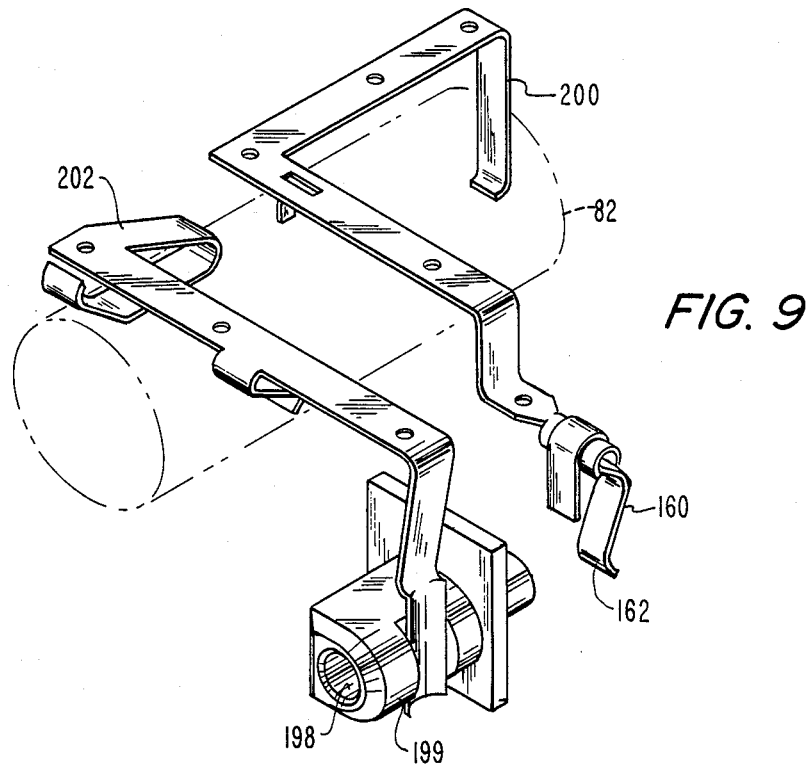
FIG. 9 is an enlarged isometric view of an electrical connection assembly shown in FIG. 3.

Also defined by the arrangement of webs 190 and as illustrated is a compartment for 82. Mounted within housing 22 and having a receptable 198 exposed to the exterior through wall portion 86 is a plug 199 for connection to a separate battery charger. For contact against one end of battery 82 is a connector 200 (FIGS. 3 and 9). Another connector 202 is correspondingly disposed so as to have one end portion engageable with the other end of battery 82 and another end portion engageable with receptacle 198. Conductive finger 160 is connected to and projects away from connector 200 so as to locate its contact member 162 alongside contact element 164. Suitable interconnecting leads as shown in FIGS. 3, 7 and 11 are included so as to complete the circuitry between battery 82, motor 58, contact element 164, charger receptable 198 and connectors 200 and 202.

In this case formed on end wall 36 of housing 22 is a protrusion 210 in which is defined a somewhat V-shaped recess 212. Recess 212 may be used to mount the entire unit, when desired, upon a matingly shaped bracket (not shown) that may be secured to a wall for more permanent installation of the appliance. For transport, the entire assemblage preferably is contained within a case provided with a plurality of recesses into which the different detachable components are seated.

Referring back to FIGS. 8 and 10, it will be noted that lower end 68 of nozzle 26 is secured with a snap fit in coupling 74 by a floating O-ring 216. The latter is captivated in the bore of coupling 74 by a retaining sleeve 218 that defines a recess. The snap fit is effected by a groove 226 formed around the terminal end portion of lower end 68.

As so far described, the assemblage is basically the same as that shown in the senior patent. For increased ruggedness, and as shown in FIG. 7, inwardly projecting ears 230 and 232 respectively protruding from shells 29 and 30 have been found to serve better for the purpose of insuring secure seating of motor 58. Ears 230 and 232 also provide obstructions that retain the motor brushes in a correct position in the presence of severe handling such as dropping of the unit. Greater reliability has been obtained by soldering a contact 234 in its connection to the motor, instead of relying on the spring-clip type of contact illustrated before. Contact 200 has been elongated and the recess defined by the associated ribs 190 and post 192 has been enlarged in order to accommodate the employment of the larger battery 82 (FIGS. 3 and 9).

The most significant change over the structure of the senior patent occurs in pump arm 106 on the exhaust side of the pump and as best shown in FIG. 6. Integrally projecting outwardly from the bottom of well 70 is a concentrically-disposed inner cylinder 240 which opens into orifice 107. O-ring 72 is captivated in place by means of a retainer 242 pressed into the interior of cylinder 240. Cylinder 240 also serves as a valve guide, accommodating a valve 244 biased or poled by a compression spring 246 disposed within cylinder 240 in a position between retainer 242 and valve 244.

In seeking to achieve a compact assemblage that was small in size compared to earlier oral irrigation appliances that served generally the same purpose, the reduced size in elevation of invertable reservoir 24 significantly reduces the head of pressure which delivers the water or other liquid from that reservoir. At the same time, the decreased overall dimensions of the unit permit use of only a comparative shorter length of stroke of piston 96 within the pump. As a result of those parameters, and in view of the normal viscosity of water or other liquid which is employed, the unit of the senior patent sometimes tended to less than optimal operation, because of the lowered pressure developed in the exhaust section as piston 96 worked to inlet a new quantity of the liquid in order to subsequently produce the next pulse delivered through nozzle 26. While that may have led to some inconsistency in the delivered pulse pressures, the primary problem was an inability of pump 28 always to prime itself properly after operation had been discontinued for a period of time. The presence of valve 244 overcomes that problem.

In use, valve 244 is maintained in the closed condition during the intake stroke during which valve 110 is pulled into the open condition. On the other hand, valve 244 opens on the exhaust stroke when valve 110 is forced into its closed condition. That is, the two valves alternate in operation with reference to the two-cycle operation of piston 96.

In view of all of the foregoing, it can be seen that progress has been made in improving the operation and reliability in performance of the apparatus of the senior patent. Importantly, the revised pump unit as particularly illustrated in FIG. 6 will prime itself even when it initially is entirely dry.

While a particular embodiment of the present invention has been shown and described, it will be obvious to those skilled in the art that changes and modifications may be made without departing from the invention in its broader aspects. Therefore, the aim in the appended claims is to cover all such changes and modifications as fall within the true spirit and scope of that which is patentable.

I claim:

1. In a device which includes a supply of liquid, a pump for propelling said liquid and means for delivering the propelled liquid to a point of use, the improvement comprising:

a housing defining a cavity within which said pump is seated;

means defining an outlet in said housing;

means defining an inlet in said housing;

said supply of liquid including a reservoir removably seated atop said housing above said pump and, when seated, sealingly coupled to said inlet;

a motor seated inside said cavity for driving said pump;

said pump having a hollow body with a chamber defined in a first portion thereof;

a piston disposed for reciprocation in said chamber with a predetermined length of stroke;

means coupled to said motor for reciprocating said piston;

means for coupling a second portion of said body to said outlet;

means for coupling a third portion of said body to said inlet;

a first check valve effectively disposed in said third portion of said body and operable to pass liquid only from said inlet to said chamber;

a second check valve effectively disposed in said second portion of said body and operable to pass liquid only from said chamber to said outlet;

said first and second check valves including respective different biasing means with said biasing means being selected to ensure that either one of said valves is closed whenever the other is open during operation of said pump;

and said outlet means including a pair of nested concentric cylinders with said second check valve being disposed within the innermost one of said cylinders.

2. A device as defined in claim 1 in which a retainer is seated in said one of said cylinders and said biasing means for said second check valve is disposed in a position between said retainer and said second check valve.

* * * * *